United States Patent [19]
Au-Young et al.

[11] Patent Number: 5,843,714
[45] Date of Patent: Dec. 1, 1998

[54] DNA ENCODING A NOVEL HUMAN PROTEOLIPID

[75] Inventors: Janice Au-Young, Berkeley; Olga Bandman, Mountain View; Surya K. Goli, Sunnyvale; Jennifer L. Hillman, San Jose, all of Calif.

[73] Assignee: Incyte Pharmaceuticals, Inc., Palo Alto, Calif.

[21] Appl. No.: 695,736

[22] Filed: Jul. 26, 1996

[51] Int. Cl.[6] .......................... C12N 15/09; C12N 15/11; C12N 15/63; C12N 5/10

[52] U.S. Cl. .................... 435/69.1; 536/23.5; 435/320.1; 435/325; 530/350

[58] Field of Search ..................................... 530/350, 359; 536/23.5; 435/320.1, 240.2, 325; 514/2

[56] References Cited

U.S. PATENT DOCUMENTS 5,508,164  4/1996  Kausch et al. ................................ 435/6

OTHER PUBLICATIONS

Stratagene (1994) pp. 154–159.
Wallace et al. (1987) Methods in Enzymology 152 : 432–442.
Fischer et al. (1994) J. Biol. Chem. 269 : 24912–24919.
Arai, H., et al., "Inhibition of the Coated Vesicle Proton Pump and Labeling of a 17,000–Dalton Polypeptide by N,N'–Dicyclohexylcarbodiimide", *J. Biol, Chem.*, 262:11006–11011 (1987).
Eytan, G.D., et al., "Selective Incorporation of Membrane Proteins into Proteoliposomes of Different Compositions", *J. Biol. Chem.*, 252:3208–3213 (1977).
Finbow, M.E., et al., "Ductin—a proton pump component, a gap junction channel and a neurotransmitter release channel", *BioEssays* 17:247–255 (1995).
Fischer, I., et al., "Expression of Plasmolipin in Oligodendrocytes", *J. Neurosci. Res.*, 28:81–89 (1991).
Krutovskikh V., et al., "Sequential changes of gap–junctional intercellular communications during multistage rat liver carcinogensis: direct measurement of communication in vivo", *Carcinogenesis*, 12:1701–1706 (1991).
Nelson, H., et al., "Molecular Cloning of cDNA Encoding the C Subunit of H[+]–ATPase from Bovine Chromaffin Granules", *J. Biol. Chem.*, 265:20390–20393 (1990).

Rancano, C., et al., "Genomic Structure and Subcellular Localization of MAL, a Human T–cell–specific Proteolipid Protein", *J. Biol. Chem.*, 269:8159–8164 (1994).
Sapirstein, V.S., et al., "Circular Dichroism and Fluorescence Studies on a Cation Channel Forming Plasma Membrane Proteolipid", *Biochemistry*, 22:3330–3335 (1983).
Sapirstein, V.S., et al., "Amyloid precursor protein is enriched in axolemma and periaxolemmal–myelin and associated clathrin–coated vesicles," *J. Neurosci. Res.*, 37:348–358 (1994).
Schaeren–Wiemers, N., et al., "Characterization of a rat gene, rMAL, encoding a protein with four hydrophobic domains in central and peripheral myelin," *J. Neurosci.*, 15:5753–5764 (1995).
Tosteson, M.T., et al., "Protein Interactions with Lipid Bilayers: The Channels of Kidney Plasma Membrane Proteolipids", *J. Membr. Biol.*, 63:77–84 (1981).
Trosko, J.E., et al., "Symposium: Cell Communication in Normal and Uncontrolled Growth", *Radiation Res.*, 123:241–251 (1990).
Zacchetti, D., et al., "VIP17/MAL, a Proteolipid in Apical Transport Vesicles", *FEBS Letters*, 377:465–469 (1995).
Marra, M. et al., (GI 1428191) EMBL Database (Accession W98280), National Center for Biotechnology Information, National Library of Medicine, Bethesda, Maryland, 20894.
Marra, M. et al., (GI 1283219) EMBL Database (Accession W12117), National Center for Biotechnology Information, National Library of Medicine, Bethesda, Maryland, 20894.

*Primary Examiner*—Stephen Walsh
*Assistant Examiner*—Michael D. Pak
*Attorney, Agent, or Firm*—Lucy J. Billings

[57] ABSTRACT

The present invention provides polynucleotides which identify and encode a novel human proteolipid (PLHu). The invention provides for genetically engineered expression vectors and host cells comprising the nucleic acid sequence encoding PLHu. The invention also provides for the use of substantially purified PLHu and its agonists in the commercial production of recombinant proteins for the treatment of diseases associated with the expression of PLHu. Additionally, the invention provides for the use of antisense molecules to PLHu in the treatment of diseases associated with the expression of PLHu. The invention also describes diagnostic assays which utilize diagnostic compositions comprising the polynucleotides which hybridize with naturally occurring sequences encoding PLHu and antibodies which specifically bind to the protein.

7 Claims, 4 Drawing Sheets

```
                                                             9                  18                  27          36          45          54
5' CCG CCA GCT CCT TCG GCA ATG AAC TTC TCC ACC AGC AGC AGC TTC GCC TAC 63                  72                  81          90          99         108
   GAC CGG GAG TTC CTC CGC ACC CTG CCC GGC TTC CTC ATC GTG GCC GAG ATC GTT
    D   R   E   F   L   R   T   L   P   G   F   L   I   V   A   E   I   V 117                 126                 135         144         153         162
   CTG GGG CTG CTG GTA ACG CTT TGG ACG CTT ATT GCT GGA ACT GAG TAC TTC CGG GTC CCC
    L   G   L   L   V   T   L   W   T   L   I   A   G   T   E   Y   F   R   V   P 171                 180                 189         198         207         216
   GCA TTT GGC TGG GTC ATG TTT GTA GCT GTA TTT TAC TGG GTC CTC ACC GTC TTC
    A   F   G   W   V   M   F   V   A   V   F   Y   W   V   L   T   V   F 225                 234                 243         252         261         270
   TTC CTC ATT ATC TAC ATA ACA ATG ACC TAC ACC AGG ATT CCC CAG GTG CCC TGG
    F   L   I   I   Y   I   T   M   T   Y   T   R   I   P   Q   V   P   W 279                 288                 297         306         315         324
   ACA ACA GTG GGC CTG TGC TTT AAC GGC AGT GCC TTC GTC TTG TAC CTC TCT GCC
    T   T   V   G   L   C   F   N   G   S   A   F   V   L   Y   L   S   A 333                 342                 351         360         369         378
   GCT GTA GAT GCA TCT TCC GTC CCT GAG AGG GAC AGT CAC AAC TTC AAC
    A   V   D   A   S   S   V   P   E   R   D   S   H   N   F   N

FIGURE 1A
```

```
            387  396  405       414       423       432
        AGC TGG GCG GCC TCA TCG TTC TTT GCC TTC CTG GTC AAC ATC TGC TAC GCT GGA
         S   W   A   A   S   S   F   F   A   F   L   V   N   I   C   Y   A   G 441            450            459       468       477       486
        AAT ACA TAT TTC AGT TTT ATA GCA TGG AGA TCC AGG ACC ATA CAG TGA TTT ACC
         N   T   Y   F   S   F   I   A   W   R   S   R   T   I   Q 495       504            513            522       531       540
        ATT TTG ATA ATT AAA AGG AAA AAA GGA AAA CTC TCA CTG TAA AAA CAG CTG 549       558            567            576       585       594
        TAG GTA TAA TGT ATA TTC CCA GAG AAT TGT ATT TAA CTA ATT AAT GTT TTT TAT 603       612            621            630       639       648
        ATT CTT AAA TTT GCT CAC AAA TTG TGG TTT GTT ACA ATT AAA CTG GAT ACT TAT 657       666            675            684       693       702
        TTG CAA AGT GTT GTA GCT TAT AAT GAA CTC TTA AGT ATC TTA ATG TAT TAA 711       720            729            738       747       756
        TGT CTT CAT AGA TCA TAT TTT CTT AGA CAA TGT TTA AAT AGA TAA ATT GCT AAT 765       774            783            792       801       810
        ATT GAG AAT GTG TCA AGT TTG TAA ACC TAA CTT TTA AGA TGC CAG ATT CTT TTT 819       828            837            846
        TGA TTA AAT GTT GCA AAA TCC CAA AAA AAA AAA AAA AAA AAA A 3'
```

FIGURE 1B

```
  1  MNFSTSSSSFAYDREF----LRTLPGFLIVAEIVLGLLVWTL  PLHu
  1  MRP-------DLGF---VRSALGVLALLQLLVLGLLVWAL    GI 1346732
  1  MAPAAATGGSTLPSGFSVFTTLPDLLFIFEFIFGGLVWIL    GI 126719

39  IAGTEYFRVPAFGWVMFVAVFYWVLTVFFLIIYITMTYTR    PLHu
 30  IADTPYHLYPAYGWVMFVAVFLWLVTIVFFIHYLFQLHMK    GI 1346732
 41  VASSLVPWPLVQGWVMFVSVFCFVATTTLIILYIIGAHGG    GI 126719

79  IPQVPWTTVGLCFNGSAFVLYLSAAVVDA-SSV--SPERD    PLHu
 70  LYMVPWPLVLLVFFVAATVLYITAFVACA--AAVDLTSLRG   GI 1346732
 81  --ETSWVTLDAAYHCTAALFYLSASVLEALATITMQDGFT    GI 126719

116  SHNFNSWAASSFFAFLVNICYAGNTYFSFIAWRSRTIQ     PLHu
109  SRPYNQRSAASFFACLVMIAYGLSAFFSFQAWRGVGSNAA    GI 1346732
119  YRHYHENIAAVVFSYIATLLYVHAVFSLIRWKS-----     GI 126719

153  TSQMAGGYS                                    PLHu
149  --------S                                    GI 1346732
153  ---------                                    GI 126719
```

FIGURE 2

DNA ENCODING A NOVEL HUMAN PROTEOLIPID

FIELD OF THE INVENTION

The present invention relates to nucleic acid and amino acid sequences of a novel human proteolipid and to the use of these sequences in the diagnosis, study, prevention and treatment of disease.

BACKGROUND OF THE INVENTION

Proteolipids are a class of hydrophobic membrane proteins characterized in part by their capacity to assume conformations compatible with solubility in organic solvents and in water (Sapirstein V. S. et al (1983) Biochemistry 22:3330–3335). This amphipathic character of proteolipids explains their participation in transmembrane ion movement. Proteolipids are components of ion channel and transport systems, such as $H^+$ channels (Arai H. et al (1987) J Biol Chem 262:11006–11011), $Ca^{2+}$ channels (Eytan G. D. et al (1977) J Biol Chem 252: 3208–3213) and the C (membrane channel) subunit of the vacuolar $H^+$-ATPase (Nelson H. et al (1990) J Biol Chem 265: 20390–20393).

The latter proteolipid, also known as ductin, is also associated with gap junctions. Gap junctions are the relatively large pores which allow free diffusion of ions across biological membranes (Finbow M. E. et al (1995) Bioessays 17:247–255). Altered gap-junction intercellular communication (GJIC) may play an essential role in cancer development. A lack of GJIC has been observed between transformed and neighboring normal cells (Trosko et al (1990) Radiation Res 123:241–251). A decrease in GJIC has also been observed within tumor cells (Krutovskikh et al (1991) Carcinogenesis 12:1701–1706).

Proteolipids are also involved in membrane vesicular trafficking. Due to their lipid-like properties, proteolipids destabilize lipid bilayers and promote membrane vesicle fusion. Such proteolipid-assisted events may include the fusions and fissions of the nuclear membrane, endoplasmic reticulum, Golgi apparatus, and various inclusion bodies (peroxisomes, lysosomes, etc).

Human T-lymphocyte maturation-associated protein (MAL), a 153 amino acid proteolipid, has been localized to the endoplasmic reticulum (ER) of T-lymphocytes, where it mediates the fusion of ER-derived vesicles and Golgi cisterna (Rancano C. et al (1994) J Biol Chem 269:8159–8164). A canine MAL homolog, VIP17, is involved in the sorting and targeting of proteins between the Golgi complex and the apical plasma membrane (Zacchetti D. et al (1995) FEBS Lett 377:465–469). A rat MAL homolog, rMAL, is expressed in the myelinating cells of the nervous system including oligodendrocytes and Schwann cells. The rMAL protein serves as a gap junction component and plays a role in myelin compaction (Schaeren-Wiemers N. et al (1995) J. Neurosci 5753–5764).

Plasmolipin from rat is a proteolipid localized to plasma membranes in kidney and brain. It has 157 amino acids and, based on hydropathy plots and secondary structure predictions, consists of four alpha-helical transmembrane domains (I through IV) of 20–22 amino acids in length. Transmembrane domains III and IV contain hydroxyl groups which may contribute to an aqueous channel. Domains I through III are connected by short hydrophilic segments of 9–11 amino acids in length, and domains III and IV are connected by a longer hydrophilic segment of 20 amino acids. The small size and high hydrophobicity of plasmolipin constrains the distribution of its transmembrane regions such that the four transmembrane alpha-helices form an antiparallel bundle, and both the amino- and carboxy-termini face the cytoplasm. This structural model defines the growing class of small hydrophobic transport-related proteolipids containing four-helix transmembrane segments, such as the MAL homologs (Rancano et al, supra), and the vacuolar $H^+$-ATPase C subunit (Nelson et al, supra).

In rat brain, plasmolipin is localized to myelinated nerve tracts, and its expression increases markedly with the onset of myelination (Fischer I. et al (1991) Neurochem Res 28:81–89). The distribution of plasmolipin within myelin appears to include regions active in membrane recycling. Endocytotic coated vesicles isolated from myelinated tracts are enriched with plasmolipin (Sapirstein V. S. (1994) J Neurosci Res 37:348–358). Incorporation of the purified rat plasmolipin protein into lipid bilayers induces voltage-dependent $K^+$ channel formation, suggesting it may function in vivo as a pore or channel (Tosteson M. T. et al (1981) J Membr Biol 63:77–84). Channel formation involved the trimerization of the plasmolipin molecule. The oligomerization model of the plasmolipin molecule portrays transmembrane domains III and IV as walls of the channel, consistent with the presence of hydroxyl groups in these domains (Sapirstein et al (1983) supra). The putative role of rat plasmolipin in transport suggests its function may be in the fluid volume regulation of the myelin complex (Fischer et al (1994), supra).

Proteolipids are involved in membrane trafficking, gap junction formation, ion transport and cellular fluid volume regulation. The selective modulation of their expression may provide a means for the regulation of vesicle trafficking or the formation of channels or gap junctions in normal as well as acute and chronic disease situations.

SUMMARY OF THE INVENTION

The present invention discloses a novel human proteolipid, hereinafter referred to as PLHu, having homology to plasmolipin from rat (*Rattus norvegicus*). Accordingly, the invention features a substantially purified proteolipid, encoded by amino acid sequence of SEQ ID NO:1, having structural characteristics of the class of proteolipids including plasmolipin.

One aspect of the invention features isolated and substantially purified polynucleotides which encode PLHu. In a particular aspect, the polynucleotide is the nucleotide sequence of SEQ ID NO:2. In addition, the invention features nucleotide sequences which hybridize under stringent conditions to SEQ ID NO:2.

The invention further relates to nucleic acid sequence encoding PLHu, oligonucleotides, peptide nucleic acids (PNA), fragments, portions or antisense molecules thereof. The present invention also relates to an expression vector which includes polynucleotide encoding PLHu and its use to transform host cells or organisms. The invention also relates to antibodies which bind specifically to the proteolipid of SEQ ID NO:1 and to a pharmaceutical composition comprising a substantially purified proteolipid of SEQ ID NO:1.

BRIEF DESCRIPTION OF THE FIGURES

FIGS. 1A and 1B show the amino acid sequence (SEQ ID NO:1) and the nucleic acid sequence (SEQ ID NO:2) of the human proteolipid PLHu, produced using MacDNAsis software (Hitachi Software Engineering Co Ltd).

FIG. 2 shows the amino acid sequence alignments among PLHu (SEQ ID NO:1), rat plasmolipin (GI 1346732; SEQ ID NO:3), and human MAL (GI 126719; SEQ ID NO:4) produced using the multisequence alignment program of DNAStar software (DNAStar Inc, Madison Wis.).

DETAILED DESCRIPTION OF THE INVENTION

Definitions

Figure 3:
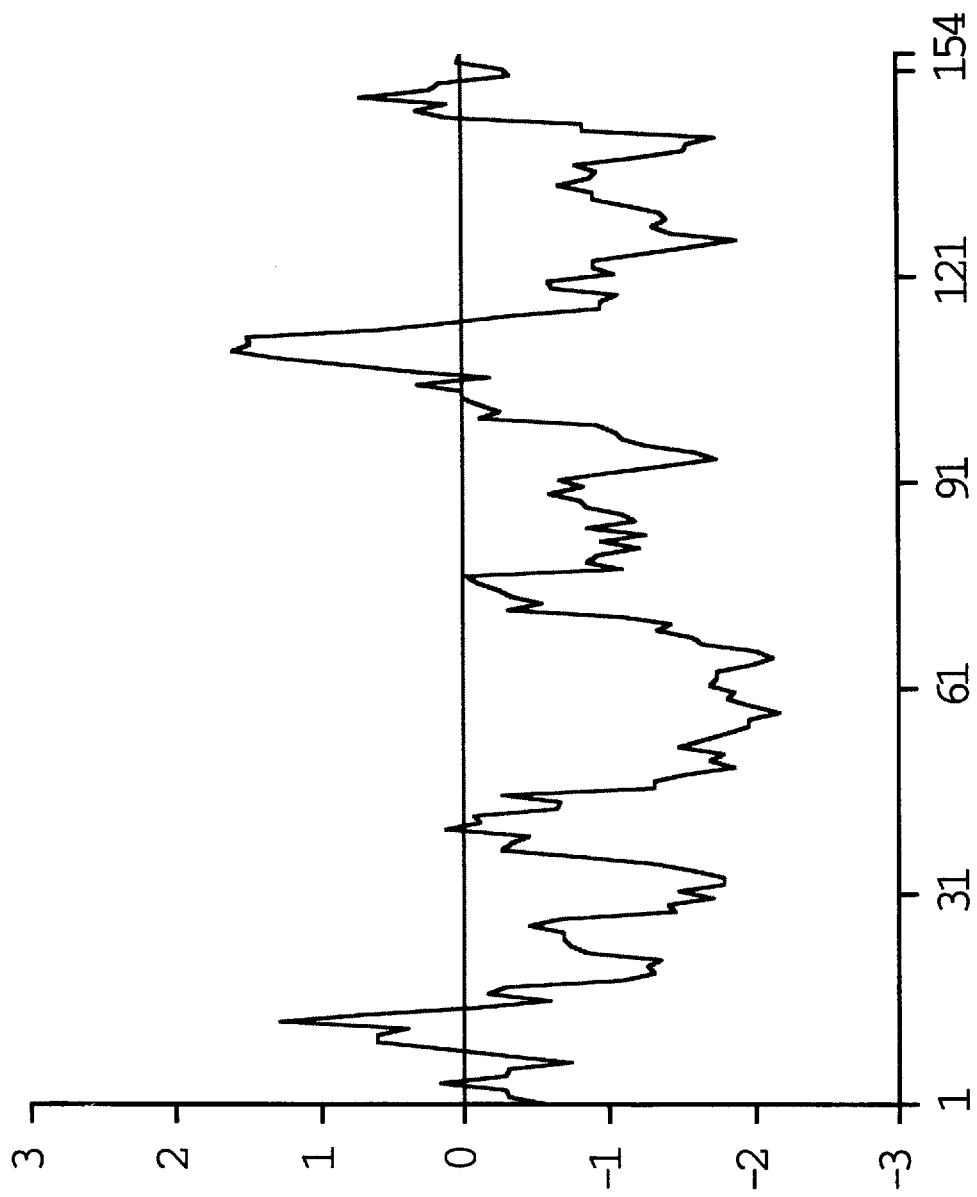
FIG. 3 shows the hydrophobicity plot (generated using MacDNAsis software) for PLHu, SEQ ID NO:1; the X axis reflects amino acid position, and the negative Y axis, hydrophobicity.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P. E. et al (1993) Anticancer Drug Des 8:53–63).

A "variant" of PLHu is defined as an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "biologically active" refers to a PLHu having structural, regulatory or biochemical functions of the naturally occurring PLHu. Likewise, "immunologically active" defines the capability of the natural, recombinant or synthetic PLHu, or any oligopeptide thereof, to induce a specific immune response in appropriate animals or cells and to bind with specific antibodies.

The term "derivative" as used herein refers to the chemical modification of a nucleic acid encoding PLHu or the encoded PLHu. Illustrative of such modifications would be replacement of hydrogen by an alkyl, acyl, or amino group. A nucleic acid derivative would encode a polypeptide which retains essential biological characteristics of natural PLHu.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm–5° C. (5° C. below the Tm of the probe) to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J. (1994) *Dictionary of Biotechnology*, Stockton Press, New York N.Y.). Amplification as carried out in the polymerase chain reaction technologies is described in Dieffenbach C. W. and G. S. Dveksler (1995, *PCR Primer, a Laboratory Manual,* Cold Spring Harbor Press, Plainview N.Y.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring PLHu.

A "substitution" results from the replacement of one or more nucleotides or amino acids by different nucleotides or amino acids, respectively.

Description

The present invention relates to a novel human proteolipid, PLHu, initially identified among the partial cDNAs from a human breast library (BRSTNOT03) and to the use of the nucleic acid and amino acid sequences disclosed herein in the study, diagnosis, prevention and treatment of disease. Northern analysis using the LIFESEQ™ database (Incyte Pharmaceuticals, Palo Alto Calif.) indicates that PLHu-encoding nucleotide sequences are also transcribed in heart atrial tissue and in lymphocytes.

The present invention also encompasses PLHu variants. A preferred PLHu variant is one having at least 80% amino acid sequence similarity to the PLHu amino acid sequence (SEQ ID NO:1), a more preferred PLHu variant is one having at least 90% amino acid sequence similarity to SEQ ID NO:1 and a most preferred PLHu variant is one having at least 95% amino acid sequence similarity to SEQ ID NO:1.

The nucleic acid sequence encoding a portion of PLHu was first identified in the cDNA, Incyte Clone 640699, through a computer-generated search for amino acid sequence alignments. The nucleic acid sequence, SEQ ID NO:2, disclosed herein (FIGS. 1A and 1B) encodes the amino acid sequence, SEQ ID NO:1, designated PLHu. The present invention is based in part on the structural homology shown in FIG. 2, among PLHu and other small proteolipids including rat plasmolipin (GI 1346732; Fischer et al (1994), supra) and human MAL (GI 126719; Rancano et al, supra).

PLHu consists of 153 amino acids and, based on the hydropathy plot (FIG. 3) and secondary structure predictions, is a member of the class of small hydrophobic transport-related proteolipids containing four alpha-helical transmembrane domains. From its homology to rat plasmolipin (FIG. 2), the transmembrane domains I to IV of PLHu are predicted to span residues 20–40, 50–72, 84–108, and 127–147, respectively. Transmembrane domains III and IV of PLHu contain a total of six ser/thr hydroxyl groups, which may form an aqueous channel. The N-terminal hydrophilic segment of PLHu is 20 amino acids, longer than the ten amino acid N-terminal segment of rat plasmolipin, and the C-terminal hydrophilic segment of PLHu is 6 amino acids, shorter than the 17 amino acid C-terminal segment of rat plasmolipin. In accordance with the structural model proposed for other small proteolipids, both the amino- and carboxy-termini of PLHu are predicted to face the cytoplasm. The short hydrophilic segments connecting domains I to II and domains II to III are 9 and 11 amino acids in length, respectively. The hydrophilic segment connecting domains III to IV is 18 amino acids in length. The human plasmolipin PLHu has 43% sequence identity with rat plasmolipin and 28% sequence identity with human MAL (FIG. 2).

The PLHu Coding Sequences

The nucleic acid and amino acid sequences of PLHu are shown in FIGS. 1A and 1B. In accordance with the invention, any nucleic acid sequence which encodes the amino acid sequence of PLHu can be used to generate recombinant molecules which express PLHu. In a specific embodiment described herein, a partial sequence of PLHu was first isolated as Incyte Clone 640699 from a human breast tissue cDNA library (BRSTNOT03).

It will be appreciated by those skilled in the art that as a result of the degeneracy of the genetic code, a multitude of PLHu-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence of naturally occurring PLHu, and all such variations are to be considered as being specifically disclosed.

Although nucleotide sequences which encode PLHu and its variants are preferably capable of hybridizing to the nucleotide sequence of the naturally occurring PLHu under appropriately selected conditions of stringency, it may be advantageous to produce nucleotide sequences encoding PLHu or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding PLHu and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a PLHu and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a gene encoding PLHu.

Also included within the scope of the present invention are polynucleotide sequences that are capable of hybridizing to the nucleotide sequence of FIGS. 1A and 1B under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and confer may be used at a defined stringency.

Altered nucleic acid sequences encoding PLHu which may be used in accordance with the invention include deletions, insertions or substitutions of different nucleotides resulting in a polynucleotide that encodes the same or a functionally equivalent PLHu. The protein may also show deletions, insertions or substitutions of amino acid residues which produce a silent change and result in a functionally equivalent PLHu. Deliberate amino acid substitutions may be made on the basis of similarity in polarity, charge, solubility, hydrophobicity, hydrophilicity, and/or the amphipathic nature of the residues as long as the biological activity of PLHu is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of PLHu. As used herein, an "allele" or "allelic sequence" is an alternative form of PLHu. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, Sequenase® (U.S. Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

Extending the Polynucleotide Sequence

The polynucleotide sequence encoding PLHu may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T. et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M. et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker J. D. et al (1991; Nucleic Acids Res 19:3055–60). Additionally, one can use PCR, nested primers and PromoterFinder libraries to walk in genomic DNA (PromoterFinder™ Clontech (Palo Alto Calif.). This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) activated, and deactivated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M. C. et al (1993) Anal Chem 65:2851–8).

Expression of the Nucleotide Sequence

In accordance with the present invention, polynucleotide sequences which encode PLHu, fragments of the polypeptide, fusion proteins or functional equivalents thereof may be used in recombinant DNA molecules that direct the expression of PLHu in appropriate host cells. Due to the inherent degeneracy of the genetic code, other DNA sequences which encode substantially the same or a functionally equivalent amino acid sequence, may be used to clone and express PLHu. As will be understood by those of skill in the art, it may be advantageous to produce PLHu-encoding nucleotide sequences possessing non-naturally occurring codons. Codons preferred by a particular prokaryotic or eukaryotic host (Murray E. et al (1989) Nuc Acids Res 17:477–508) can be selected, for example, to increase the rate of PLHu expression or to produce recombinant RNA transcripts having desirable properties, such as a longer half-life, than transcripts produced from naturally occurring sequence.

The nucleotide sequences of the present invention can be engineered in order to alter a coding sequence of PLHu for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant nucleotide sequence encoding PLHu may be ligated to a heterologous sequence to encode a fusion protein. For example, for screening of peptide libraries for inhibitors of PLHu activity, it may be useful to encode a chimeric PLHu protein that is recognized by a commercially available antibody. A fusion protein may also be engineered to contain a cleavage site located between a PLHu sequence and the heterologous protein sequence, so that the PLHu may be cleaved and substantially purified away from the heterologous moiety.

In an alternate embodiment of the invention, the coding sequence for PLHu may be synthesized, whole or in part, using chemical methods well known in the art (see Caruthers M. H. et al (1980) Nuc Acids Res Symp Ser 215–23, Horn T. et al (1980) Nuc Acids Res Symp Ser 225–32, etc). Alternatively, the protein itself could be produced using chemical methods to synthesize a PLHu amino acid sequence, whole or in part. For example, peptide synthesis can be performed using various solid-phase techniques (Roberge J. Y. et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles,* W. H. Freeman and Co, New York N.Y.). The composition of the synthetic peptides may be confirmed by amino acid analysis or sequencing (eg, the Edman degradation procedure; Creighton, supra). Additionally the amino acid sequence of PLHu, or any part thereof, may be altered during direct synthesis and/or combined using chemical methods with sequences from other proteins, or any part thereof, to produce a variant polypeptide.

Expression Systems

In order to express a biologically active PLHu, the nucleotide sequence encoding PLHu or its functional equivalent, is inserted into an appropriate expression vector, ie, a vector which contains the necessary elements for the transcription and translation of the inserted coding sequence.

Methods which are well known to those skilled in the art can be used to construct expression vectors containing a PLHu coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual,* Cold Spring Harbor Press, Plainview N.Y. and Ausubel F. M. et al (1989) *Current Protocols in Molecular Biology,* John Wiley & Sons, New York N.Y.

A variety of expression vector/host systems may be utilized to contain and express a PLHu coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla Calif.) or pSport1 (Gibco BRL) and ptrp-lac hybrids and the like may be used. The baculovirus polyhedrin promoter may be used in insect cells.

Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of PLHu, vectors based on SV40 or EBV may be used with an appropriate selectable marker.

In bacterial systems, a number of expression vectors may be selected depending upon the use intended for PLHu. For example, when large quantities of PLHu are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the PLHu coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding PLHu may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J. 6:307–311). Alternatively, plant promoters such as the small subunit of RUBISCO (Coruzzi et al (1984) EMBO J. 3:1671–1680; Broglie et al (1984) Science 224:838–843); or heat shock promoters (Winter J. and Sinibaldi R. M. (1991) Results Probl Cell Differ 17:85–105) may be used. These constructs can be introduced into plant cells by direct DNA transformation or pathogen-mediated transfection. For reviews of such techniques, see Hobbs S. or Murry L. E. in McGraw Hill *Yearbook of Science and Technology* (1992) McGraw Hill New York N.Y., pp 191–196 or Weissbach and Weissbach (1988) *Methods for Plant Molecular Biology,* Academic Press, New York N.Y., pp 421–463.

An alternative expression system which could be used to express PLHu is an insect system. In one such system, *Autographa californica* nuclear polyhedrosis virus (AcNPV) is used as a vector to express foreign genes in *Spodoptera frugiperda* cells or in Trichoplusia larvae. The PLHu coding sequence may be cloned into a nonessential region of the virus, such as the polyhedrin gene, and placed under control of the polyhedrin promoter. Successful insertion of the PLHu coding sequence will render the polyhedrin gene inactive and produce recombinant virus lacking coat protein coat. The recombinant viruses are then used to infect *S. frugiperda* cells or Trichoplusia larvae in which PLHu is expressed (Smith et al (1983) J Virol 46:584; Engelhard E. K. et al (1994) Proc Nat Acad Sci 91:3224–7).

In mammalian host cells, a number of viral-based expression systems may be utilized. In cases where an adenovirus is used as an expression vector, a coding sequence for PLHu may be ligated into an adenovirus transcription/translation complex consisting of the late promoter and tripartite leader sequence. Insertion in a nonessential E1 or E3 region of the viral genome will result in a viable virus capable of expressing PLHu in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a PLHu sequence. These signals include the ATG initiation codon and adjacent sequences. In cases where nucleic acid encoding PLHu, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D. et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express PLHu may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M. et al (1977) Cell 11:223–32) and adenine phosphoribosyltransferase (Lowy I. et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M. et al (1980) Proc Natl Acad Sci 77:3567–70); npt, which confers resistance to the aminoglycosides neomycin and G-418 (Colbere-Garapin F.

et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S. C. and R. C. Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C. A. et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the PLHu polynucleotide sequence is inserted within a marker gene sequence, recombinant cells containing PLHu can be identified by the absence of marker gene function. Alternatively, a marker gene can be placed in tandem with a PLHu sequence under the control of a single promoter. Expression of the marker gene in response to induction or selection usually indicates expression of the tandem PLHu as well.

Alternatively, host cells which contain the coding sequence for PLHu and express PLHu may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding PLHu can be detected by DNA-DNA or DNA-RNA hybridization or amplification using probes, portions or fragments of PLHu-encoding nucleotides. Nucleic acid amplification based assays involve the use of oligonucleotides or oligomers based on the PLHu sequence to detect transformants containing PLHu DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of PLHu, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on PLHu is preferred, but a competitive binding assay may be employed. These and other assays are described, among other places, in Hampton R. et al (1990, *Serological Methods, a Laboratory Manual*, APS Press, St Paul Minn.) and Maddox D. E. et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to PLHu include oligolabeling, nick translation, end-labeling or PCR amplification using a labeled nucleotide. Alternatively, the PLHu sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and U.S. Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 incorporated herein by reference.

Purification of PLHu

Host cells transformed with a PLHu-encoding nucleotide sequence may be cultured under conditions suitable for the expression and recovery of the encoded protein from cell culture. The protein produced by a recombinant cell may be contained intracellularly or secreted depending on the sequence and/or the vector used. As will be understood by those of skill in the art, expression vectors containing PLHu can be designed for efficient production and proper transmembrane insertion of PLHu into a prokaryotic or eukaryotic cell membrane. Other recombinant constructions may join PLHu to nucleotide sequence encoding a polypeptide domain which will facilitate purification of soluble proteins (Kroll D. J. et al (1993) DNA Cell Biol 12:441–53; cf discussion of vectors infra containing fusion proteins).

PLHu may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and PLHu is useful to facilitate purification. One such expression vector provides for expression of a fusion protein compromising an PLHu and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263–281) while the enterokinase cleavage site provides a means for purifying the proteolipid from the fusion protein.

In addition to recombinant production, fragments of PLHu may be produced by direct peptide synthesis using solid-phase techniques (cf Stewart et al (1969) *Solid-Phase Peptide Synthesis,* W. H. Freeman Co, San Francisco; Merrifield J. (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of PLHu may be chemically synthesized separately and combined using chemical methods to produce the full length molecule.

Uses of PLHu

The rationale for the use of polynucleotide and polypeptide sequences disclosed herein is based in part on the structural homology among the novel PLHu and small proteolipids including rat plasmolipin and human MAL.

Exocytosis facilitated by PLHu may influence membrane trafficking within the cell and affect the release of chemokines involved in cell migration, proteases which are active in inflammation or other similar activities involving endothelial cells, fibroblasts, lymphocytes, etc. Therefore, a diagnostic test for altered expression of PLHu can accelerate diagnosis and proper treatment of conditions caused by viral or other infections, traumatic tissue damage, hereditary diseases such as arthritis or asthma, invasive leukemias and lymphomas; or other physiologic/pathologic problems associated with abnormal membrane trafficking.

Gap junctions are important in regulating metabolic communication and cooperation among cells. Altered gap-junction intercellular communication (GJIC) may play an essential role in cancer development. A lack of GJIC has been observed between transformed and neighboring normal cells. In addition, a decrease in GJIC has also been observed within tumor cells. A diagnostic test for decreased PLHu expression may therefore correlate with tumorigenesis.

In cardiac muscle fibers, gap junctions permit the unimpeded diffusion of ions from one cell to another. Thus cardiac cells are so interconnected that, for example, when one atrial cell becomes excited, the action potential quickly spreads to all of the cells in the atrial syncytium. A diagnostic test for abnormal PLHu expression in heart may be correlated with abnormal propagation of action potentials in aging cardiac muscle fibers, for example in cardiac arrhythmia. In such instances it may be advantageous to suppress PLHu expression. PLHu expression could be suppressed by administration of PLHu antisense oligonucleotides. Alternatively, specific antibodies against PLHu, or inhibitors of PLHu such as channel blockers, may be introduced to treat diseases or conditions associated with abnormal PLHu expression.

Due to their lipid-like properties, proteolipids destabilize lipid bilayers and promote membrane vesicle fusion. PLHu may therefore be incorporated into liposomes or artificial vesicles to promote vesicle fusion for drug delivery.

PLHu Antibodies

PLHu-specific antibodies are useful for the diagnosis of conditions and diseases associated with expression of PLHu. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

PLHu for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of PLHu amino acids may be fused with those of another protein such as keyhole limpet hemocyanin and antibody produced against the chimeric molecule. Procedures well known in the art can be used for the production of antibodies to PLHu.

For the production of antibodies, various hosts including goats, rabbits, rats, mice, etc may be immunized by injection with PLHu or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to PLHu may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R. Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce PLHu-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G. and Milstein C. (1991; Nature 349:293–299).

Antibody fragments which contain specific binding sites for PLHu may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W. D. et al (1989) Science 256:1275–1281).

A variety of protocols for competitive binding or immunoradiometric assays using either polyclonal or monoclonal antibodies with established specificities are well known in the art. Such immunoassays typically involve the formation of complexes between PLHu and its specific antibody and the measurement of complex formation. A two-site, monoclonal-based immunoassay utilizing monoclonal antibodies reactive to two noninterfering epitopes on a specific PLHu protein is preferred, but a competitive binding assay may also be employed. These assays are described in Maddox D. E. et al (1983, J Exp Med 158:1211).

Diagnostic Assays Using PLHu Specific Antibodies

Particular PLHu antibodies are useful for the diagnosis of conditions or diseases characterized by expression of PLHu or in assays to monitor patients being treated with PLHu, agonists or inhibitors. Diagnostic assays for PLHu include methods utilizing the antibody and a label to detect PLHu in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring PLHu, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on PLHu is preferred, but a competitive binding assay may be employed. These assays are described, among other places, in Maddox, D. E. et al (1983, J Exp Med 158:1211).

In order to provide a basis for diagnosis, normal or standard values for PLHu expression must be established. This is accomplished by combining body fluids or cell extracts taken from normal subjects, either animal or human, with antibody to PLHu under conditions suitable for complex formation which are well known in the art. The amount of standard complex formation may be quantified by comparing various artificial membranes containing known quantities of PLHu with both control and disease samples from biopsied tissues. Then, standard values obtained from normal samples may be compared with values obtained from samples from subjects potentially affected by disease. Deviation between standard and subject values establishes the presence of disease state.

Drug Screening

PLHu, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between PLHu and the agent being tested, may be measured.

Another technique for drug screening which may be used for high throughput screening of compounds having suitable binding affinity to the PLHu is described in detail in "Determination of Amino Acid Sequence Antigenicity" by Geysen H. N., WO Application 84/03564, published on Sept. 13, 1984, and incorporated herein by reference. In summary, large numbers of different small peptide test compounds are synthesized on a solid substrate, such as plastic pins or some other surface. The peptide test compounds are reacted with fragments of PLHu and washed. Bound PLHu is then detected by methods well known in the art. Substantially purified PLHu can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding PLHu specifically compete with a test compound for binding PLHu. In this manner, the antibodies can be used to detect the presence of any peptide which shares one or more antigenic determinants with PLHu.

Uses of the Polynucleotide Encoding PLHu

A polynucleotide encoding PLHu, or any part thereof, may be used for diagnostic and/or therapeutic purposes. For diagnostic purposes, the PLHu of this invention may be used to detect and quantitate gene expression in biopsied tissues in which expression of PLHu may be implicated. The diagnostic assay is useful to distinguish between absence, presence, and excess expression of PLHu and to monitor regulation of PLHu levels during therapeutic intervention.

Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding PLHu or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring PLHu, alleles or related sequences.

Probes may also be used for the detection of related sequences and should preferably contain at least 50% of the nucleotides from any of these PLHu encoding sequences. The hybridization probes of the subject invention may be derived from the nucleotide sequence of SEQ ID NO:2 or from genomic sequence including promoter, enhancer elements and introns of the naturally occurring PLHu. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

Other means for producing specific hybridization probes for PLHu DNAs include the cloning of nucleic acid sequences encoding PLHu or PLHu derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostics

Polynucleotide sequences encoding PLHu may be used for the diagnosis of conditions or diseases with which the expression of PLHu is associated. For example, polynucleotide sequences encoding PLHu may be used in hybridization or PCR assays of fluids or tissues from biopsies to detect PLHu expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The PLHu nucleotide sequence disclosed herein provide the basis for assays that detect activation or induction associated with inflammation or disease. The PLHu nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of PLHu nucleotide sequences in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for PLHu expression must be established. This is accomplished by combining body fluids or cell extracts taken from normal subjects, either animal or human, with PLHu, or a portion thereof, under conditions suitable for hybridization or amplification. Standard hybridization may be quantified by comparing the values obtained for normal subjects with a dilution series of PLHu run in the same experiment where a known amount of substantially purified PLHu is used. Standard values obtained from normal samples may be compared with values obtained from samples from patients afflicted with PLHu-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

Polymerase Chain Reaction (PCR) as described in U.S. Pat. Nos. 4,683,195 and 4,965,188 provides additional uses for oligonucleotides based upon the PLHu sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P. C. et al 1993 J Immunol Methods 159:235–44) or biotinylating (Duplaa C. et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to the gene encoding rat plasmolipin and its expression profile, the PLHu polynucleotide disclosed herein may provide the basis for the design of molecules for the treatment of diseases such as cardiac arrhythmia.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense PLHu. See, for example, the techniques described in Sambrook et al (supra) and Ausubel et al (supra).

The polynucleotides comprising full length cDNA sequence and/or its regulatory elements enable researchers to use PLHu as an investigative tool in sense (Youssoufian H. and H. F. Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding PLHu can be turned off by transfecting a cell or tissue with expression vectors which express high levels of a desired PLHu fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I., personal communication) and even longer if appropriate replication elements are part of the vector system.

As mentioned above, modifications of gene expression can be obtained by designing antisense molecules, DNA, RNA or PNA, to the control regions of PLHu, ie, the promoters, enhancers, and introns. Oligonucleotides derived from the transcription initiation site, eg, between –10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J. E. et al (In: Huber B. E. and B. I. Carr (1994) *Molecular and Immunologic Approaches,* Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of RNA encoding PLHu.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding PLHu. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences for PLHu disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for PLHu can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C. M. (1993; Blood Rev 7:127–34) and Trask B. J. (1991; Trends Genet 7:149–54).

The technique of fluorescent in situ hybridization of chromosome spreads has been described, among other places, in Verma et al (1988) *Human Chromosomes: A Manual of Basic Techniques,* Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a PLHu on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example, an STS based map of the human genome was recently published by the Whitehead-MIT Center for Genomic Research (Hudson T. J. et al (1995) *Science* 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of PLHu, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

The examples below are provided to illustrate the subject invention and are not included for the purpose of limiting the invention.

EXAMPLES

I cDNA Library Construction

The BRSTNOT03 cDNA library was constructed from nontumorous breast tissue removed from a 54-year-old Caucasian female (specimen #0025B; Mayo Clinic, Rochester, Minn.) who had undergone bilateral radical mastectomy following diagnosis of residual invasive grade 3 of 4 mammary ductal adenocarcinoma. The pathology report indicated that the biopsied fibroadipose tissue from the right breast was negative for tumor. Tumor cells forming a nodule 1×0.7×0.7 cm were identified in the right breast. The remaining breast parenchyma exhibited proliferative fibrocystic changes without atypia. The skin, nipple, and fascia were uninvolved. One of 10 axillary lymph nodes was involved with metastatic tumor, as a microscopic, intranodal focus. Prior to surgery, the patient was prescribed estrogen as part of postmenopausal hormone replacement therapy.

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.0, precipitated using 0.3M sodium acetate and 2.5 volumes of ethanol, resuspended in RNAse-free water, and DNase treated at 37° C. The RNA extraction was repeated with acid phenol pH 4.0 and precipitated with sodium acetate and ethanol as before. The mRNA was then isolated using the Qiagen Oligotex kit (QIAGEN, Inc.; Chatsworth, Calif.) and used to construct the cDNA library.

The mRNA was handled according to the recommended protocols in the SuperScript Plasmid System for cDNA Synthesis and Plasmid Cloning (Cat. #18248-013; Gibco/BRL). cDNAs were fractionated on a Sepharose CL4B column (Cat. #275105-01; Pharmacia), and those cDNAs exceeding 400 bp were ligated into pSport I. The plasmid pSport I was subsequently transformed into DH5a™ competent cells (Cat. #18258-012; Gibco/BRL).

II Isolation and Sequencing of cDNA Clones

Plasmid DNA was released from the cells and purified using the REAL Prep 96 Plasmid Kit for Rapid Extraction Alkaline Lysis Plasmid Minipreps (Catalog #26173; QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, LIFE TECHNOLOGIES™) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 40° C.

The cDNAs were sequenced by the method of Sanger et al. (1975, J. Mol Biol 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III Homology Searching of cDNA Clones and Their Deduced Proteins

Each cDNA was compared to sequences in GenBank using a search algorithm developed by Applied Biosystems and incorporated into the INHERIT- 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S. F. (1993) J Mol Evol 36:290–300; Altschul, S. F. et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al. supra).

Analogous computer techniques use BLAST (Altschul S. F. 1993 and 1990, supra) to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of PLHu to Full Length or to Recover Regulatory Elements

The nucleic acid sequence encoding full length PLHu (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known PLHu nucleotide sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook J. et al, supra). After incubation for one hour at 37° C., the whole transformation mixture is plated on Luria Bertani (LB)-agar (Sambrook J. et al, supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [$\gamma$-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The nucleotide sequence encoding PLHu, or any part thereof, is used to inhibit in vivo or in vitro expression of naturally occurring PLHu. Although use of antisense oligonucleotides, comprising about 20 base-pairs, is specifically described, essentially the same procedure is used with larger cDNA fragments. An oligonucleotide based on the coding sequence of PLHu as shown in FIGS. 1A and 1B is used to inhibit expression of naturally occurring PLHu. The complementary oligonucleotide is designed from the most unique 5' sequence as shown in FIGS. 1A and 1B and used either to inhibit transcription by preventing promoter binding to the upstream nontranslated sequence or translation of an PLHu transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A and 1B.

VIII Expression of PLHu

Expression of PLHu is accomplished by subcloning the cDNAs into appropriate vectors and transfecting the vectors into host cells. In this case, the cloning vector, pSport, previously used for the generation of the cDNA library is used to express PLHu in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length PLHu. The signal sequence directs the secretion of PLHu into the bacterial growth media which can be used directly in the following assay for activity.

IX PLHu Activity

The pore-forming ability of PLHu is assayed by monitoring its effect on transmembrane pH gradients in liposomes. Mitochondrial cytochrome C oxidase, a proton pump, is reconstituted into liposomes by sonication. The pH-sensitive fluorescent dye pyranine (Eastman Kodak) is then incorporated into the proteoliposomes by rapid freeze-thawing and sonication. Excess dye is removed by centrifugation and resuspension of the liposomes into an appropriate buffer. Addition of ascorbate and cytochrome C initiates proton uptake into the liposomes. PLHu is added and proton efflux is monitored by the fluorescence changes arising from changes in internal pH of the liposomes at excitation and emission wavelengths of 460 nm and 508 nm, respectively.

Lipid bilayer destabilization promoted by PLHu, incorporated into membranes by expression or by reconstitution, is assayed by measurement of the fluorescence polarization of the lipophilic dye 1,6-diphenyl-1,3,5-hexatriene (Eastman Kodak) inserted into the membranes.

X Production of PLHu Specific Antibodies

PLHu substantially purified using PAGE electrophoresis (Sambrook, supra) is used to immunize rabbits and to produce antibodies using standard protocols. The amino acid sequence translated from PLHu is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIG. 3) is described by Ausubel F. M. et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F. M. et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring PLHu Using Specific Antibodies

Naturally occurring or recombinant PLHu is substantially purified by immunoaffinity chromatography using antibodies specific for PLHu. An immunoaffinity column is constructed by covalently coupling PLHu antibody to an activated chromatographic resin such as CnBr-activated Sepharose (Pharmacia Biotech). After the coupling, the resin is blocked and washed according to the manufacturer's instructions.

Cellular fractions from cells containing PLHu are prepared by solubilization of the whole cell and isolation of subcellular fractions by differential centrifugation, by the addition of detergent, or by other methods well known in the art. Alternatively, soluble PLHu containing a signal sequence may be secreted in useful quantity into the medium in which the cells are grown.

A fractionated PLHu-containing preparation is passed over the immunoaffinity column, and the column is washed under conditions that allow the preferential absorbance of PLHu (eg, high ionic strength buffers in the presence of detergent). The column is eluted under conditions that disrupt antibody/PLHu binding (eg, a buffer of pH 2–3 or a high concentration of a chaotrope such as urea or thiocyanate ion), and PLHu is collected.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A substantially purified polypeptide comprising the amino acid sequence of SEQ ID NO:1.

2. An isolated and purified polynucleotide sequence consisting of a nucleic acid sequence encoding the polypeptide of claim 1.

3. The polynucleotide sequence of claim 2 consisting of the sequence of SEQ ID NO:2 or degenerate variants thereof.

4. An expression vector containing the polynucleotide sequence of claim 2.

5. An isolated host cell comprising the expression vector of claim 4.

6. A method for producing a polypeptide comprising the amino acid sequence shown in SEQ ID NO:1, the method comprising the steps of:

a) culturing the host cell of claim 5 under conditions suitable for the expression of the polypeptide; and b) recovering the polypeptide from the host cell culture.

7. An isolated and purified polynucleotide sequence fully complementary to the sequence of SEQ ID NO:2 or degenerate variants thereof.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 153 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: BRSTNOT03
        ( B ) CLONE: 640699

( x i ) SEQUENCE DESCRIPTION: SEQ ID NO:1:

```
Met Asn Phe Ser Thr Ser Ser Ser Ser Phe Ala Tyr Asp Arg Glu Phe
1               5                   10                  15

Leu Arg Thr Leu Pro Gly Phe Leu Ile Val Ala Glu Ile Val Leu Gly
            20                  25                  30

Leu Leu Val Trp Thr Leu Ile Ala Gly Thr Glu Tyr Phe Arg Val Pro
        35                  40                  45

Ala Phe Gly Trp Val Met Phe Val Ala Val Phe Tyr Trp Val Leu Thr
    50                  55                  60

Val Phe Phe Leu Ile Ile Tyr Ile Thr Met Thr Tyr Thr Arg Ile Pro
65                  70                  75                  80

Gln Val Pro Trp Thr Thr Val Gly Leu Cys Phe Asn Gly Ser Ala Phe
                85                  90                  95

Val Leu Tyr Leu Ser Ala Ala Val Val Asp Ala Ser Ser Val Ser Pro
            100                 105                 110

Glu Arg Asp Ser His Asn Phe Asn Ser Trp Ala Ala Ser Ser Phe Phe
            115                 120                 125

Ala Phe Leu Val Asn Ile Cys Tyr Ala Gly Asn Thr Tyr Phe Ser Phe
    130                 135                 140

Ile Ala Trp Arg Ser Arg Thr Ile Gln
145                 150
```

( 2 ) INFORMATION FOR SEQ ID NO:2:

( i ) SEQUENCE CHARACTERISTICS:
        ( A ) LENGTH: 853 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: BRSTNOT03
        ( B ) CLONE: 640699

( x i ) SEQUENCE DESCRIPTION: SEQ ID NO:2:

```
CCGCCAGCTC CTTCGGCAAT GAACTTCTCC ACCAGCAGCA GCAGCTTCGC CTACGACCGG      60
GAGTTCCTCC GCACCCTGCC CGGCTTCCTC ATCGTGGCCG AGATCGTTCT GGGGCTGCTG     120
GTATGGACGC TTATTGCTGG AACTGAGTAC TTCCGGGTCC CCGCATTTGG CTGGGTCATG     180
TTTGTAGCTG TATTTTACTG GGTCCTCACC GTCTTCTTCC TCATTATCTA CATAACAATG     240
ACCTACACCA GGATTCCCCA GGTGCCCTGG ACAACAGTGG GCCTGTGCTT TAACGGCAGT     300
GCCTTCGTCT TGTACCTCTC TGCCGCTGTT GTAGATGCAT CTTCCGTCTC CCCTGAGAGG     360
GACAGTCACA ACTTCAACAG CTGGGCGGCC TCATCGTTCT TTGCCTTCCT GGTCAACATC     420
TGCTACGCTG GAAATACATA TTTCAGTTTT ATAGCATGGA GATCCAGGAC CATACAGTGA     480
TTTACCATTT TGATAATTAA AAGGAAAAAA AAAGGAAGAC TCTCACTGTA AAAACAGCTG     540
TAGGTATAAT GTATATTCCC AGAGAATTGT ATTTAACTAA TTAATGTTTT TTATATTCTT     600
AAATTTGCTC ACAAATTGTG GTTTGTTACA ATTAAACTGG ATACTTATTT GCAAAGTGTT     660
GTAGCTTATA ATGAACTCTT AAGTATCTTA TTAATGTATT AATGTCTTCA TAGATCATAT     720
TTTCTTAGAC AATGTTTAAA TAGATAAATT GCTAATATTG AGAATGTGTC AAGTTTGTAA     780
ACCTAACTTT TAAGATGCCA GATTCTTTTT TGATTAAATG TTGCAAAATC CCAAAAAAAA     840
AAAAAAAAAA AAA                                                        853
```

(2) INFORMATION FOR SEQ ID NO:3:

(i) SEQUENCE CHARACTERISTICS:
        (A) LENGTH: 157 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1346732

(xi) SEQUENCE DESCRIPTION: SEQ ID NO:3:

```
Met Arg Pro Asp Leu Gly Phe Val Arg Ser Ala Leu Gly Val Leu Ala
 1               5                  10                  15
Leu Leu Gln Leu Val Leu Gly Leu Leu Val Trp Ala Leu Ile Ala Asp
            20                  25                  30
Thr Pro Tyr His Leu Tyr Pro Ala Tyr Gly Trp Val Met Phe Val Ala
            35                  40                  45
Val Phe Leu Trp Leu Val Thr Ile Val Phe Phe Ile Ile Tyr Leu Phe
        50                  55                  60
Gln Leu His Met Lys Leu Tyr Met Val Pro Trp Pro Leu Val Leu Leu
 65                 70                  75                  80
Val Phe Phe Val Ala Ala Thr Val Leu Tyr Ile Thr Ala Phe Val Ala
                85                  90                  95
Cys Ala Ala Ala Val Asp Leu Thr Ser Leu Arg Gly Ser Arg Pro Tyr
                100                 105                 110
Asn Gln Arg Ser Ala Ala Ser Phe Phe Ala Cys Leu Val Met Ile Ala
            115                 120                 125
Tyr Gly Leu Ser Ala Phe Phe Ser Phe Gln Ala Trp Arg Gly Val Gly
        130                 135                 140
Ser Asn Ala Ala Thr Ser Gln Met Ala Gly Gly Tyr Ser
145                 150                 155
```

(2) INFORMATION FOR SEQ ID NO:4:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 126719

(xi) SEQUENCE DESCRIPTION: SEQ ID NO:4:

```
Met Ala Pro Ala Ala Ala Thr Gly Gly Ser Thr Leu Pro Ser Gly Phe
 1               5                  10                  15
Ser Val Phe Thr Thr Leu Pro Asp Leu Leu Phe Ile Phe Glu Phe Ile
            20                  25                  30
Phe Gly Gly Leu Val Trp Ile Leu Val Ala Ser Ser Leu Val Pro Trp
            35                  40                  45
Pro Leu Val Gln Gly Trp Val Met Phe Val Ser Val Phe Cys Phe Val
        50                  55                  60
Ala Thr Thr Thr Leu Ile Ile Leu Tyr Ile Ile Gly Ala His Gly Gly
 65                 70                  75                  80
Glu Thr Ser Trp Val Thr Leu Asp Ala Ala Tyr His Cys Thr Ala Ala
                85                  90                  95
```

-continued

| Leu | Phe | Tyr | Leu 100 | Ser | Ala | Ser | Val | Leu 105 | Glu | Ala | Leu | Ala | Thr 110 | Ile | Thr |
| Met | Gln | Asp 115 | Gly | Phe | Thr | Tyr | Arg 120 | His | Tyr | His | Glu | Asn 125 | Ile | Ala | Ala |
| Val | Val 130 | Phe | Ser | Tyr | Ile | Ala 135 | Thr | Leu | Leu | Tyr | Val | Val 140 | His | Ala | Val |
| Phe 145 | Ser | Leu | Ile | Arg | Trp 150 | Lys | Ser | Ser | | | | | | | |